US00PP37208P3

(12) United States Plant Patent
Clarkson

(10) Patent No.: US PP37,208 P3
(45) Date of Patent: Jan. 13, 2026

(54) ***FRAGARIA* PLANT NAMED 'PGP182'**

(50) Latin Name: ***Fragaria* x *ananassa***
Varietal Denomination: PGP182

(71) Applicant: Graham Clarkson, Faversham (GB)

(72) Inventor: Graham Clarkson, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 19/070,802

(22) Filed: Mar. 5, 2025

(65) Prior Publication Data

US 2025/0366383 P1 Nov. 27, 2025

(30) Foreign Application Priority Data

May 24, 2024 (QZ) ..... PBR 20241190

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209, 208
CPC ..... A01H 5/08; A01H 5/00; A01H 6/4709; A01H 6/74; A01H 6/7409
See application file for complete search history.

(56) References Cited

U.S. PATENT DOCUMENTS

PP32,418 P2 * 11/2020 Vinson ..... A01H 6/7409 Plt./209

* cited by examiner

*Primary Examiner* — June Hwu
(74) *Attorney, Agent, or Firm* — Penny J. Aguirre

(57) ABSTRACT

A new cultivar of *Fragaria* plant named 'PGP182' that is characterized by its fruit that is consistently large throughout the season, its fruit that is medium red in color, highly glossy and juicy, its fruit that has a high brix and a distinct, floral flavor, its fruit that primarily displays achenes below the fruit surface, and its dense plants that are strong in vigor with day-neutral fruit bearing.

3 Drawing Sheets

Botanical classification: *Fragaria* x *ananassa.*
Variety denomination: 'PGP182'.

CROSS-REFERENCE TO RELATED APPLICATIONS

This application claims priority to European Community Plant Variety Office (CPVO) Plant Breeder's Rights Application No. 2024/1190 filed on May 24, 2024, under 35 U.S.C. 119(f), the entire contents of which is incorporated by reference herein. This application is also related to plant breeders' rights application in The United Kingdom on Sep. 27, 2024, application No. 10/201, and a plant breeders' rights application in Canada on Jan. 17, 2025, application No. 25-11910. The Applicant received the information for the Plant breeders' rights applications directly from the Inventor.

BACKGROUND OF THE INVENTION

The present invention relates to a new and distinct cultivar of *Fragaria*, botanically known as *Fragaria* x *ananassa* 'PGP182' and will be referred to hereafter by its cultivar name, 'PGP182'. 'PGP182' is a day neutral strawberry plant primarily adapted to the climate and growing conditions of the United Kingdom and other regions of similar climate and day length for use in the fresh fruit market.

The new cultivar was derived from an ongoing breeding program conducted by the Inventor at a greenhouse in Faversham, Kent, United Kingdom. The goal of the breeding program was to develop a new cultivar of *Fragaria* with large fruit having high yields, uniform shape, firm skin, low acid content, good eating quality, and consistent cropping combined with high disease tolerance. 'PGP182' arose from a controlled cross made by the Inventors in February of 2017 between an unpatented selection from the Inventor's breeding program, designated as accession number 'GB96', as the female parent and an unpatented selection from the Inventor's breeding program, designated as accession number 'CC45', as the male parent. 'PGP182' was selected as a single unique plant in Sint-Truiden, Belgium in summer of 2018 from amongst the seedlings that resulted from the above cross.

Asexual propagation of the new cultivar was first accomplished by rooting stolons in Faversham, Kent, United Kingdom in summer of 2018. Asexual propagation by rooting of stolons and tissue culture using meristematic tissue has shown that the unique characteristics of the new cultivar are stable and reproduced true to type in successive generations.

SUMMARY OF THE INVENTION

The following traits have been repeatedly observed and represent the characteristics of the new cultivar. These attributes in combination distinguish 'PGP182' as a unique cultivar of *Fragaria.*

1. 'PGP182' exhibits fruit that is consistently large in size throughout the season.

2. 'PGP182' exhibits fruit that is medium red in color, highly glossy, and juicy.
3. 'PGP182' exhibits fruit that has a high brix reading and a distinct floral flavor.
4. 'PGP182' exhibits fruit that primarily displays achenes below the fruit surface.
5. 'PGP182' exhibits dense plants that are strong in vigor with day-neutral fruit bearing.

The female parent of 'PGP182' differs from 'PGP182' in having smaller fruit with achenes that are less indented in the fruit and a lower yield. The male parent of 'PGP182' differs from 'PGP182' in having fruit that is paler in color, no aromatic notes, and a lower yield.

'PGP182' can be compared to the *Fragaria* cultivar 'Eves Delight 2' (U.S. Plant Pat. No. 32,418) and 'Eves Joy' (U.S. Plant Pat. No. 35,911). Both 'PGP182' and 'Eves Delight 2' produce large fruit throughout the season. 'Eves Delight 2' exhibits fruit that is conical while 'PGP182' exhibits fruit with a reniform shape. The fruit of 'PGP182' is glossier and juicier than that of 'Eves Delight 2' and has a lower acidity. The fruit of 'Eves Delight 2' is sweeter than 'PGP182' and has a higher brix content but lacks the distinct floral flavor of 'PGP182'. 'PGP182' and 'Eves Delight 2' have even color across the fruit skin, however 'PGP182' has a stronger and brighter red color than 'Eves Delight 2'. The fruit skin of 'PGP182' is less firm than that of 'Eves Delight 2', however 'PGP182' still performs well in 7-day shelf-life testing that assesses bruising, glossiness and color changes. 'Eves Delight 2' produces fruit earlier in the season than 'PGP182', however 'PGP182' has a higher overall yield.

The plant of 'Eves Delight 2' is generally taller and wider in size than 'PGP182'. 'PGP182' also has a denser canopy than 'Eves Delight 2' and a higher number of flowers per truss than 'Eves Delight 2'. The leaves of 'PGP182' show no interveinal blistering throughout the season, while 'Eves Delight 2' shows medium blistering. Both varieties have leaves rounded at the apex, obtuse at the base and are greater in length than width, though the leaves of 'PGP182' are slightly larger overall. The leaves of 'Eves Delight 2' are paler in color than those of 'PGP182'. Both varieties have mostly concave leaves with serrate to crenate margins. The petioles are similar in size for both 'PGP182' and 'Eves Delight 2', however the petiolules of 'PGP182' are shorter than those of 'Eves Delight 2'.

Both 'PGP182' and 'Eves Delight 2' display their inflorescence level with the plant canopy, however 'PGP182' also presents some inflorescence beneath and above the canopy. The calyx is similar in size in both varieties, however the calyx of 'Eves Delight 2' is generally smaller than the corolla while it is generally larger or the same size for 'PGP182'. The petals of both varieties are similar in their size and number, however those of 'PGP182' are slightly larger overall. Both varieties have rounded petals overall, with the base being more acute in 'PGP182'. The petals of 'Eves Delight 2' are non-overlapping while 'PGP182' has some overlapping petals. The calyx is mostly upwards and recurved relative to the fruit in both 'PGP182' and 'Eves Delight 2'. A band without achenes is absent or very narrow in both varieties and both present achenes below the surface. 'PGP182' has fewer seeds per berry than 'Eves Delight 2'.

'Eves Joy' is similar to 'PGP182' in having fruit with a medium to high glossy surface and achenes that are primarily presented below the surface. 'Eves Joy' differs from 'PGP182' in having a smaller plant size, a less dense plant canopy, fruit that is larger in size, and fruit that is more conical in shape.

BRIEF DESCRIPTION OF THE DRAWINGS

The accompanying color photographs illustrate the overall appearance and distinct characteristics of the new *Fragaria*. The photographs were taken of 3-month-old plants of 'PGP182' as grown on table-tops in coir bags under tunnels with polyethylene covers in Faversham, Kent, United Kingdom.

The photograph in FIG. 1 provides a view of 'PGP182' bearing fruit.

Figure 1:
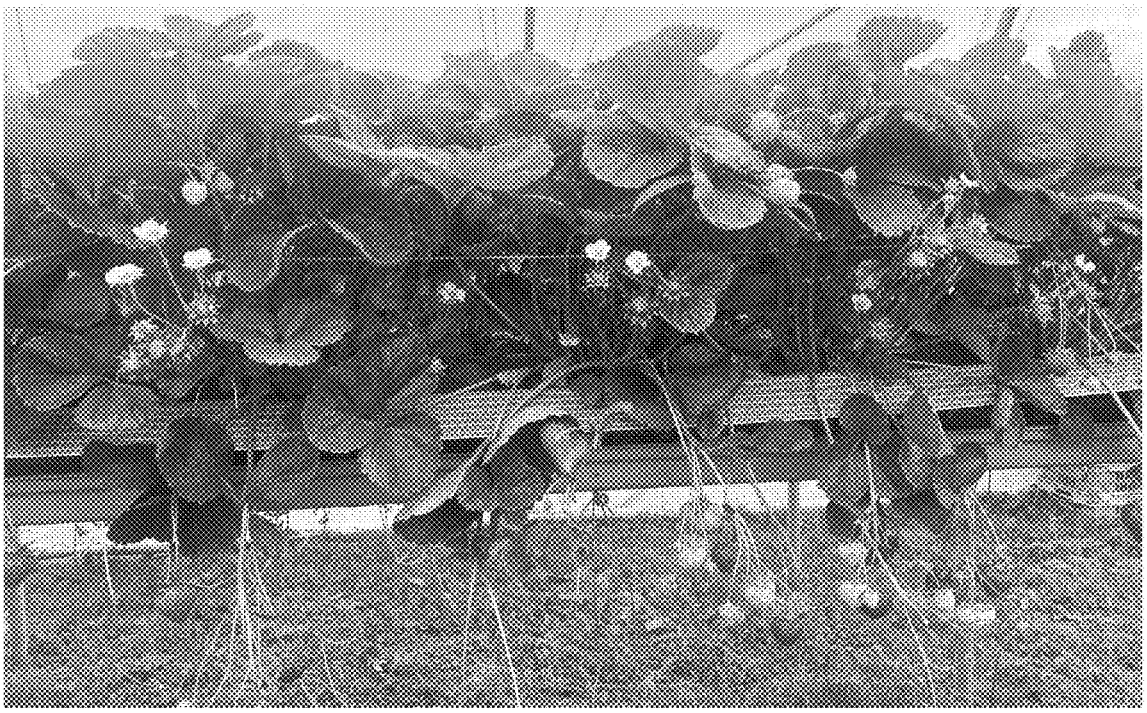
Figure 2:
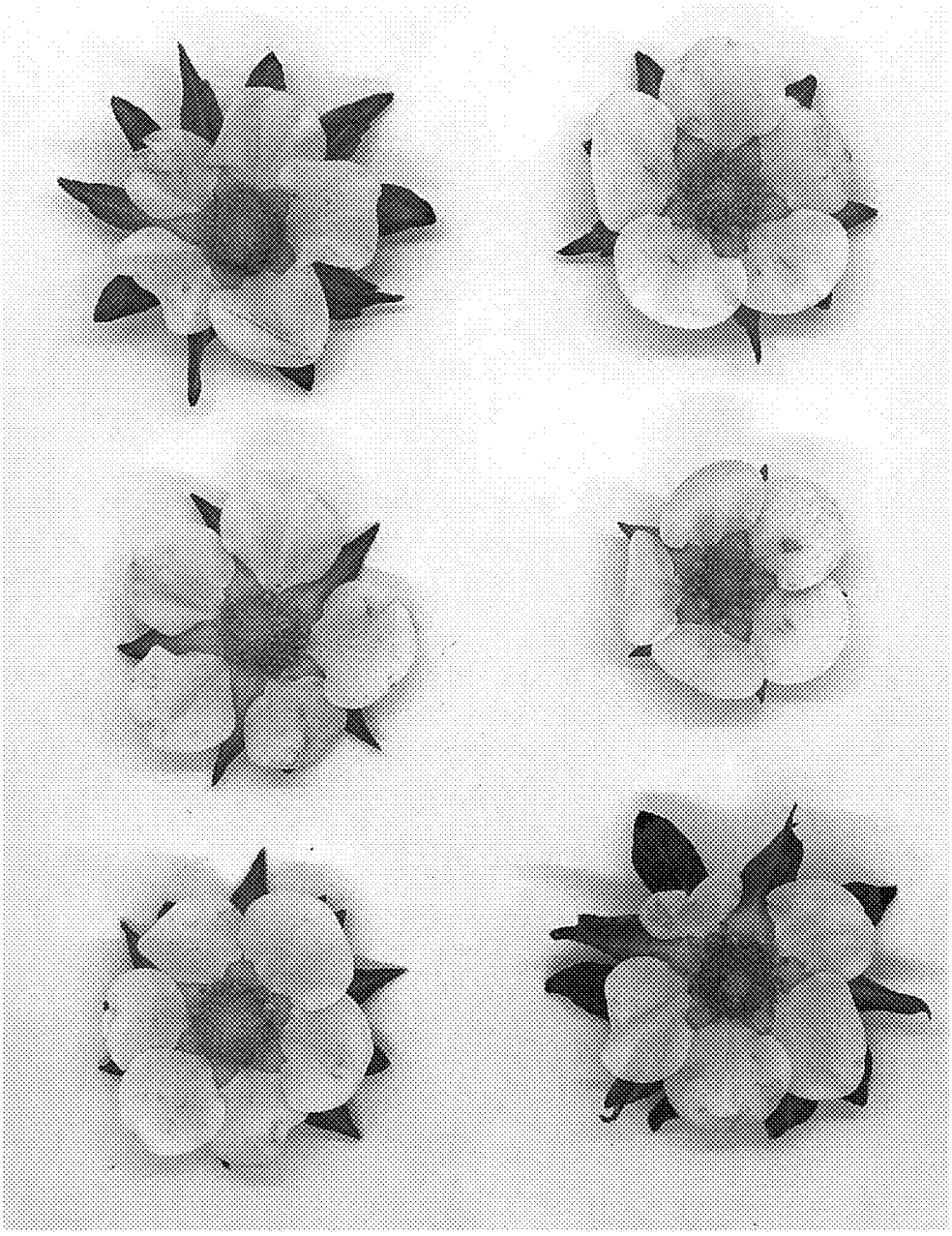

The photograph in FIG. 2 provides a close-up view of the flowers of 'PGP182'.

Figure 3:
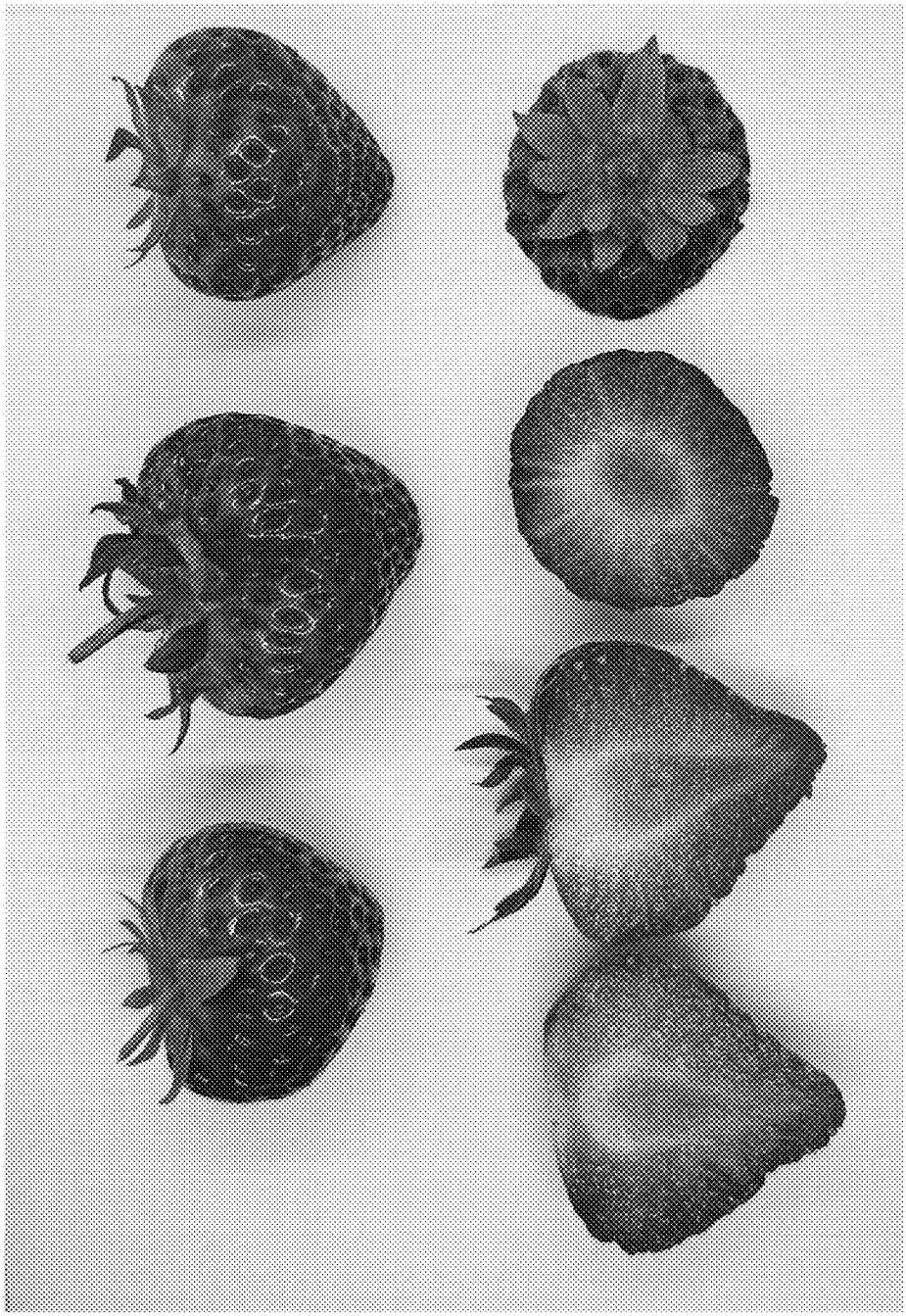

The photograph in FIG. 3 provides a close-up view of the whole fruit of 'PGP182' (left) and longitudinal and horizontal cross sections (right) of the fruit.

The colors in the photographs are as close as possible with the photographic and printing technology utilized and the color values cited in the detailed botanical description accurately describe the colors of the new *Fragaria*.

BOTANICAL DESCRIPTION OF THE PLANT

The following is a detailed description of 3-month-old plants of 'PGP182' as grown outdoors on tabletops in coir bags, under polyethylene tunnels in Faversham, Kent, United Kingdom. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—April throughout the summer in Faversham, Kent, The United Kingdom.

*Plant type*.—Herbaceous fruit producing perennial.

*Plant habit*.—Semi-upright with medium to high density and strong vigor.

*Height and spread*.—Medium to large spread, reaching an average height of 39 cm and an average width of 8 cm as a 3-month-old plant.

*Cold hardiness*.—Not tested in areas where temperatures below 32° F. occur.

*Diseases and pests*.—Tolerant to *Botryotinia cinerea* and slight susceptibility to *Podosphaera leucotricha* (powdery mildew) as observed under conditions in Faversham, Kent, the United Kingdom, no susceptibility or resistance to pests has been observed.

*Root description*.—Fibrous, NN155D in color.

*Root development*.—An average of 2 weeks to initiate roots and 5 weeks to produce a young rooted plant from a rooted cutting.

*Propagation*.—Rooting of stolons and tissue culture.

*Growth rate*.—Vigorous.

*Stem description*.—Acaulescent.

*Stolon description*.—An average of 2 stolons per plants with 5 nodes per stolon, average of 40 cm in length, sparsely pubescent, 150B in color with weak to medium anthocyanin coloration.

Foliage description:

*Leaf division*.—Three leaflets.

*Leaf arrangement*.—Basal.

*Leaf attachment*.—Petiolate.
*Leaflet shape*.—Rounded.
*Leaf size*.—Average of 13 cm in length and 22 cm in width.
*Leaflet size*.—Terminal leaflet; an average length of 12 cm and 11 cm in width, lateral leaflets; an average of 11.3 cm in length and 1 cm in width.
*Leaflet margins*.—Serrate to crenate, with an average of 20 serrations per leaf.
*Leaflet base*.—Rounded to acute.
*Leaflet apex*.—Round.
*Leaflet glossiness*.—Upper surface low, lower surface dull.
*Leaflet aspect*.—Mostly concave with some flat.
*Leaflet interveinal blistering*.—Absent.
*Leaflet venation*.—Pinnate, coloration matches leaflet color.
*Leaflet surface*.—Upper surface mostly glabrous with light pubescence at the margins, lower surface slightly pubescent along the veins.
*Leaflet color*.—Both surfaces 147A.
*Petiole*.—Round in shape with an average length of 23.3 cm and average width of 4.9 mm, 145A in color, weak to moderate pubescence with hairs being both horizontal and slightly upwards in attitude.
*Petiolules*.—Round in shape with an average length of 1.82 cm and an average width of 2.79 mm, 145B in color, surface pubescence is moderate.
*Stipule*.—Average length of 3.27 cm and average width of 1.2 cm, 54B in color.

Flower description:
*Inflorescence*.—Truss.
*Inflorescence size*.—Average of 13.5 cm in length and 22.9 cm in width.
*Flower initiation and expression conditions*.—Temperature dependent.
*Time of flowering* (50% *of plants at first flower*).—Early season.
*Flower position relative to foliage*.—Mostly beneath and level with the leaf canopy, some above.
*Flower size*.—3.1 cm.
*Flower number per truss*.—Average of 6 flowers.
*Flower fragrance*.—Weak-typical of species.
*Calyx*.—Average of 3.3 cm in diameter, generally the same size or slightly larger than the corolla, horizontal or upwards in attitude.
*Sepals*.—Average of 11 per flower, acute apex and obtuse base, adaxial color; 141A to 141B, abaxial color; 143A to 143B.
*Sepal position*.—Mostly level with the fruit shoulder and some raised.
*Petals*.—5 to 8, average of 1.2 cm in length and 1.4 cm in width, rounded in shape with an acute base, rounded apex and entire margins, petals are overlapping and non- overlapping in arrangement, upper and lower surface glabrous, 155A in color.
*Peduncles*.—Moderate pubescence that is slightly upwards in attitude, 145A in color, average of 19.1 cm in length and 4.6 mm in width.
*Pedicels*.—Moderate pubescence that is mostly upwards in attitude, average of 7 cm in length and 2.1 mm in width, 145B in color.
*Bracts*.—Observed on majority of the flower trusses at the point of branching from early developmental stage, which progresses into a small single leaflet as the truss matures and fruit develops, average of 4.8 cm in length and 2.8 cm in width, 147A in color, upper surface mostly glabrous with light pubescence at the margins, lower surface slightly pubescent along the veins.

Reproductive organs:
*Gynoecium*.—Average of 5.4 mm in height and 7 mm in width, rounded dome shape, apocarpus with multiple simple carpels present with capitate shaped stigma.
*Androecium*.—Stamens; average of 19 per flower, shape is a cone-like tube that is wider at the base, anthers; oval, average of 1.47 mm in length, 12A in color, pollen; moderate in quantity, 2A in color.

Fruit description:
*Shape*.—Mostly conical-reniform, shape is similar for primary, secondary and tertiary fruit, apex is primarily obtuse and at the calyx is primarily retuse when excluding the neck.
*Season of harvest*.—May to the end of October in Faversham, Kent, the United Kingdom.
*Time of ripening* (50% *of plants with first ripe fruit*).—Early.
*Type of bearing*.—Day neutral.
*Size*.—Large with an average of 4.1 cm in length and 4.2 cm in width, an average length to width ratio of roughly 1:1.
*Surface*.—Smooth with medium-strong glossiness.
*Calyx position*.—Mostly upwards and recurved with some level to the fruit.
*Attitude of calyx segments*.—Upwards and outwards.
*Diameter of calyx relative to fruit diameter*.—Smaller, same size and larger.
*Glossiness*.—Even and medium to strong.
*External color* (*skin*).—N34A, retained throughout cropping season.
*Internal color* (*flesh*).—Near flesh; 44B, near core; 35C.
*Evenness of color of skin*.—Very even.
*Evenness of color of flesh*.—Paler at the core and center.
*Acidity*.—Low with total titratable acid (TTA), an average of 0.53% over three seasons in trials.
*Sweetness*.—High.
*Soluble solids*.—Brix value of 9.
*Firmness*.—Skin is medium-firm; flesh is medium.
*Juiciness*.—High.
*Aroma*.—Medium.
*Weight*.—Average of 19.5 g per berry and 1,810 g per plant from late May to end of October over three seasons in trials.
*Number of fruit per plant*.—Average of 93 from late May to end of October over three seasons in trials.
*Hollow center*.—Slight on primary, secondary and tertiary fruit.
*Shelf life*.—Very good, at least 7 days in cold storage.
*Achene color*.—154B.
*Achene position*.—Below and level to the surface.
*Achene number*.—An average of 185.6 per berry.
*Band without achenes*.—Mostly absent or narrow.
*Shipping quality*.—High.
*Market use*.—Fresh fruit consumption.

It is claimed:

1. A new and distinct cultivar of *Fragaria* plant named 'PGP182' substantially as herein illustrated and described.

* * * * *